United States Patent [19]

Crosson et al.

[11] Patent Number: 4,966,577
[45] Date of Patent: Oct. 30, 1990

[54] PREVENTION OF LENS-RELATED TISSUE GROWTH IN THE EYE

[75] Inventors: Craig E. Crosson, The Woodlands, Tex.; Beverly E. Barton, West Orange, N.J.; William H. Garner, Corona Del Mar; Arlene E. Gwon, Newport Beach, both of Calif.

[73] Assignee: Allergan, Inc., Irvine, Calif.

[21] Appl. No.: 168,697

[22] Filed: Mar. 16, 1988

[51] Int. Cl.$^5$ ........................ A61N 1/30; A61M 31/00
[52] U.S. Cl. ........................................ 604/20; 604/49; 514/912
[58] Field of Search ............................ 604/20, 49, 172; 514/912-915; 424/85; 436/547-548; 530/387-389, 849; 435/172.2, 68

[56] References Cited

U.S. PATENT DOCUMENTS

| | | | |
|---|---|---|---|
| 4,363,758 | 12/1982 | Musuko et al. | 424/85 |
| 4,432,751 | 2/1984 | Emery et al. | 604/49 |
| 4,657,930 | 4/1987 | Emery et al. | 514/912 |
| 4,665,089 | 5/1987 | Siezen et al. | 514/912 |
| 4,778,815 | 10/1988 | Cash | 514/912 |
| 4,778,828 | 10/1988 | Palmai et al. | 514/912 |
| 4,797,422 | 1/1989 | Testa | 514/912 |
| 4,826,872 | 5/1989 | Terao et al. | 514/474 |
| 4,871,350 | 10/1989 | Lam | 604/49 |

FOREIGN PATENT DOCUMENTS

| | | | |
|---|---|---|---|
| 1178206 | 11/1984 | Canada | 514/912 |
| 2110532 | 6/1983 | United Kingdom | 514/912 |

OTHER PUBLICATIONS

Heath et al., "Antibody-Targeted Liposomes: Increase in Specific Toxicity of Methotrexate γ-Aspartate", Proc. Natl. Sci., vol. 80, 3/83, 1377-1381.

Campbell, "Monoclonal Antibody Technology," *Laboratory Techniques in Biochemistry and Molecular Biology*, vol. 13, pp. 16-25.

Cole et al., "Enzymatic Zonulolysis and Cryoextraction of Cataracts", International Surgery, Sep. 1968, vol. 50, No. 3, pp. 242-244.

Kincses et al., "Experimental Production of Antibodies Against Cataractous Human Lens", Acta Medica Acad. Sci., vol. 31(1-2), pp. 9-13 (1974).

Russell et al., "The Development of a Monoclonal Antibody to a Human Gamma Crystallin", Current Eye Research, vol. 3, No. 11, 1984, pp. 1329-1335.

Nissen et al., "Antibodies to Lens Antigens in Cataract and After Cataract Surgery", British J. of Ophthal., vol. 65, 1981, pp. 63-66.

Mulders et al., *Curr. Eye Res.*, 7: 207 (1988).

Avrameas et al., *Immunochemistry* 8: 1175-1179 (1971).

Nakane et al., *Jour. of Histochem. Cytochem.* 22: 1084-1091 (1974).

Monji et al., *Biochem. Biophs. Res. Comm.* 85: 671 (1978).

Deguchi, T. et al., *Cancer Res.* 46: 3751-3755 (1986).

Ghose, T. et al., *Europe J. Cancer* 11: 321-326 (1975).

Youle, R. et al., *Proc. Nat'l. Acad. Sci. USA* 77: 5483-5486 (1980).

Hurwitz, E. et al., *Cancer Res.* 35: 1175-1181 (1975).

Mills, S. et al., *Hybridoma* 5: 265-275 (1986).

Pimm, M. et al., *Int. J. Cancer* 30: 75 (1982).

Paul and Goodenough, *J. Cell. Biol.* 96: 625 (1983).

Fazekas et al., *J. Immunol. Methods* 35: 1 (1980).

*Primary Examiner*—C. Fred Rosenbaum
*Assistant Examiner*—Sharon Rose
*Attorney, Agent, or Firm*—Knobbe, Martens, Olson & Bear

[57] ABSTRACT

Disclosed is a composition for preventing secondary cataract formation in the eye following removal of the lens, comprising an antibody specific to particular lens cells related to secondary cataract formation, which antibody is conjugated to an antiproliferative agent. The particularly preferred antiproliferative agents require activation after binding of the antibody to the target cells, and activation may be accomplished by addition of a second composition or by exposure of the eye to electromagnetic energy.

Also disclosed is a method of using the composition by administering it directly to the site from which the lens was removed to kill or prevent proliferation of lens cells.

29 Claims, No Drawings

PREVENTION OF LENS-RELATED TISSUE GROWTH IN THE EYE

BACKGROUND OF THE INVENTION

The present invention relates to a method and composition for preventing the ingrowth of intraocular tissue, and in particular discloses means for preventing growth of lens fiber cells and fibroblast-type cells in a lens capsule after surgical removal of the lens.

Surgical removal of the lens from the lens capsule and insertion of an intraocular lens is commonly indicated as treatment for cataracts. In this procedure, complete removal or destruction of all lens cells and epithelial cells in the lens capsule is imperative if complications are to be avoided. One of the most common complications of this type is ingrowth of lens cells or other cells in the lens capsule following intraocular lens implantation.

"Secondary cataract" formation is a proliferation of cells occurring within the year following surgery in approximately 17—30% of patients receiving intraocular lenses. In subsequent years, the percentage of patients experiencing such ingrowth increases.

The secondary cataract formation generally results from the migration of lens epithelial cells into the posterior capsule with the proliferation of cortical material (Elschnig pearls). Any cellular proliferation in the lens capsule is to be avoided if secondary cataract formation is to be prevented. Every effort is made, of course, during the phacoemulsification or extracapsular with aspiration and irrigation procedure utilized to remove the natural lens, to completely remove all lens cells, lens fiber cells, and/or epithelial cells that may subsequently proliferate and form secondary cataracts. However, these efforts, to date, have not been entirely successful, due primarily to the fragmentation of the lens tissue during surgical removal and the difficulty of removing every lensrelated cell.

Extracapsular cataract extraction and implantation of intraocular lenses are being performed at ever increasing rates in the United States. Well over 1 million such procedures are performed every year, and as the retirementage population increases, the incidence of such procedure is also expected to increase.

Accordingly, there is a great need for an effective and simple procedure for ensuring the complete removal and/or destruction of lens cells and other proliferative cells from the lens capsule prior to implantation of the intraocular lens.

BRIEF DESCRIPTION OF THE INVENTION

The present invention relates to an immunotoxin, comprising an antibody specific to the proliferative cells to be destroyed. The antibody is conjugated to an antiproliferative agent. The antiproliferative agent may be a simple toxin, which acts directly and immediately on the cells to which the antibody becomes bound. Alternatively, in a preferred embodiment of the invention, the antiproliferative agent requires an external agent for activation and formation of the actual cytotoxic agent. This external activation may be photo-optical activation, or may comprise the addition of one or more cooperative compounds which act with the conjugated antiproliferative agent to produce an active cell-killing or growth-arresting moiety.

Thus, in accordance with one embodiment of the invention, there is provided a composition for preventing intraocular tissue ingrowth following removal of the natural lens, comprising an antibody that is specific to an epithelial cell surface antigen of proliferative cells in the lens capsule, but not specific to other ocular tissue; and an antiproliferative agent conjugated to the antibody for killing or arresting the growth of the proliferative cells. In one preferred embodiment the antibody is polyclonal antibody; in another, it is monoclonal antibody. In other preferred embodiments, the antibody is specific to lens epithelial cell surface antigens, and/or to lens fiber cell surface antigens A particularly preferred type of antiproliferative agent must be activated in order to exhibit cytotoxic properties. This activation may require cooperation with a second compound to form a cytotoxic species, or may require activation by exposure to light. The antiproliferative agent may further generate an oxidizing agent when activated, such as hydroxy radical, superoxide radical, singlet oxygen, or peroxide anion. The agent requiring activation may be an enzyme, and the second compound required for activation may be a substrate for the enzyme, wherein action of the enzyme on the substrate generates the cytotoxic species. Examples of suitable enzymes are glucose oxidase, xanthine oxidase, NADPH oxidase, lactate oxidase (*Aerococcus viridans*), and methanol oxidase (*Hansenula polymorpha*), which act on their respective substrates glucose, purines (xanthine or, in special cases, acetaldehyde), NADPH, lactate, and lower alkyl alcohol to create oxidizing moieties. Photoactivated molecules that create toxic agents upon activation by exposure to light include methylene blue, hematoporphyrin, chlorpromazine, and promazine. These photoactivated molecules generally release heat upon activation, which is itself believed to have an antiproliferative effect.

The present invention also includes a method for preventing intraocular lens-associated tissue growth in the eye, comprising the steps of providing an antibody specific to proliferative cells in the lens capsule or the posterior chamber or the eye, but not to other eye tissue, wherein the antibody is conjugated to an antiproliferative agent, introducing the antibody directly into the lens capsule after removal of the natural lens therefrom, permitting the antibody to bind to proliferative cells in the lens capsule, and killing the bound proliferative cells with the antiproliferative agent. Where activation of the antiproliferative agent by light or by the addition of a second compound is required, the method also includes such activation after binding the antibody to the target cells, such as by directing light into the lens capsule or the posterior chamber, or by adding the second compound to the site of the bound antibody.

Unlike other "magic bullet" antibody conjugate therapeutic procedures, clearance of the antibody by the liver and liver toxicity are not problems with the present invention because of the localized administration of the antibody conjugate.

Moreover, the photoactivation of antibody-linked antiproliferative agent in the present invention is eminently more advantageous than in prior art procedures involving treatment of relatively opaque tissue. The tissue involved in the treatments described herein is, of course, optically transparent.

Other objects, features, and advantages of the present invention will become apparent from the detailed description of the invention that follows.

DETAILED DESCRIPTION OF THE INVENTION

A. Isolation of Antigen and Preparation of Antibody

Appropriate antibodies for utilization in the present invention may be produced using conventional polyclonal and/or monoclonal antibody-generation procedures. Certain antibodies specific to surface proteins of proliferative cells in the lens capsule are known. See, for example, U.S. Pat. No. 4,432,751 (the disclosure of which is incorporated by this reference), which discloses an antibody specific to lens epithelial cells that mediates the destruction of those cells in the presence of complement.

In general, appropriate antibodies may be prepared by immunizing a mammal with appropriate cell surface antigen from the target proliferative cells. Conventional techniques may then be used to either isolate polyclonal antibody from the animal, or to generate monoclonal antibody in accordance with the currently well-known hybridoma techniques pioneered by Kohler and Milstein, *Nature* 256: 495–497 (1975).

We have isolated two lens fiber cell proteins of 26,000 and 70,000 daltons, which we have denominated, respectively, MP26 and MP70. These proteins were isolated from rabbit lens cells. (It should be noted that MP26 is highly conserved between species, so the antibodies to that protein will be useful in humans.) Another protein, MP17, has been identified and reported in the literature, and monoclonal antibody to that antigen is also reported. Mulders, et al., *Curr. Eve Res.* 7:207 (1988). This antibody may be used in the practice of the current invention.

The total lens-associated protein (including lens fiber cell protein and lens epithelial cell protein) was successfully used as antigen to develop polyclonal antibody in rabbits. Rabbits were immunized by an injection of antigen, followed by hyperimmunization after one week. When the titer of antibody to the antigen had been permitted to develop to the desired level, serum was collected from which the antibody was purified.

Antibody was purified from serum in a two-step process. First, an affinity column was prepared comprising covalently bound lens-associated protein. The column removed antibody from the serum that was specific to lensassociated protein. This antibody fraction was then eluted from the column, and a second column comprising other ocular tissue antigen, specifically corneal endothelium, ciliary body, and trabecular meshwork was used to remove antibody that had affinity for these other antigens. The resulting antibody was specific to the lens-associated cell antigen, but not to other ocular antigen. Polyacrylamide gel electrophoresis and Western blot analysis were used to characterize the specificity of the purified serum. This serum was selective for only lens specific antigens, and was used to isolate the antigen of interest by binding the antibody in a column and passing a solution of lens cell protein through the column. The eluate primarily comprised two proteins, the MP26 and MP70 previously discussed. (It should be noted that MP26 and MP70 are localized only in the differentiated lens fiber cell, and are not found in the lens epithelial cells. Other antibodies may be developed in a similar manner that are specific to lens epithelial cells.)

Because of the interspecies conservation of MP26, antibodies to rabbit MP26 are believed to be useful against human MP26. Of course, by substituting human antigen, the procedures described herein may be utilized to generate anti-human antibodies. Accordingly, the invention specifically contemplates antibodies against human lens fiber cell and human lens epithelial cell antigen.

This polyclonal antibody may be used directly to form the conjugates of the present invention.

Although polyclonal antibody of the type described herein is suitable for use in accordance with this invention to prevent proliferation of lens fiber cells, and polyclonal antibody may also be used against lens epithelial cells, monoclonal antibody is preferred because of its higher specificity, consistency from batch to batch, and (with the right antibody) its total lack of reactivity with any other tissue than the target cells.

Appropriate monoclonal antibodies may be prepared by injecting the isolated MP26 or MP70 antigen (or other suitable animal or human antigen) into mice to generate an immune response, sacrificing the animals and removing the spleen, separating the spleen cells and fusing them with murine myeloma cells using Sendai virus or polyethylene glycol, and then plating out and growing up hybridoma colonies. The hybridomas are then screened for crossreactivity with lens epithelial cell surface epitopes (This screening procedure preferably involves labeling the antibody from the hybridoma with a detectable label, such as a radiolabel or fluorescein isothiocyanate, and contacting epithelial cells with the labeled antibody to determine whether the antibody binds to the cell.) Selected clones are then grown either in vitro or as a tumor in mice with compatible transplantation Ags, and monoclonal antibody is collected from the serum or ascites fluid of the animals.

Although the description, for convenience, centers around antibody to "a" cell, it will be understood that the antibody used in the present invention may actually be a mixture of antibodies specific to all of the target proliferative cells. Thus, for example, it may be desirable to provide one antibody to differentiated lens fiber cells, and another to lens epithelial cells.

B. Selection of Antiproliferative Agent

In general, there are two major categories of antiproliferative agents that may be used in practicing the present invention. These categories are direct acting agents and agents requiring "activation." As used herein, "antiproliferative agents" requiring "activation" shall broadly include agents that themselves become cytotoxic upon subjection to an outside influence (such as electromagnetic radiation or another compound), and agents that participate in the generation of a separate cytotoxic moiety upon subjection to an outside influence.

Agents that require activation are preferred, because their cytotoxic effect can be regulated and timed to precisely obtain only the desired effect by controlling the activation thereof. Thus, an antibody conjugate of this type of antiproliferative agent can be injected or otherwise placed in the anterior chamber of the eye after removal of the natural lens, the antibody can be given time to bind to the target cells, and then the antiproliferative agent can be activated.

One type of agent that is particularly suitable and preferred is that category that generates an oxidizing moiety upon activation. We have found oxidative action to be especially effective in preventing proliferation of cells that cause secondary cataract formation.

Particularly preferred antiproliferative agents of this type include enzymes, such as oxidase enzymes, and photoactivated compounds, such as hematoporphyrin. The active cytotoxic agent generated by these preferred antiproliferative agents may be hydrogen peroxide, superoxide ion, hydroxy radical, or other agent capable of causing oxidative damage. The production of heat is a byproduct of these reactions. These oxidative moieties have been identified to cause lysis of lens epithelial cells. Two important components of some of these interactions have been identified: $H_2O_2$ and $O_2-$. $H_2O_2$ effectively interacts with $O_2-$ to form hydroxy radicals. The $O_2-$ is formed either by interaction of light with molecular oxygen in the presence of photosensitizers, or by reduction of molecular oxygen by enzymes to form $O_2-$ or $H_2O_2$.

Preferred photosensitizing or photoactivated antiproliferative agents for conjugation to the antibodies of the present invention include hematoporphyrin, chlorpromazine, and promazine. Hematoporphyrin absorbs at a maximum of 395 and 500–600 nm. Accordingly, activation of hematoporphyrin utilizing laser light of a wavelength within that range is particularly preferred.

Oxidizing enzymes that may be useful in the practice of the present invention include methanol oxidase, NADPH oxidase, lactate oxidase, xanthine oxidase, and glucose oxidase. These "antiproliferative agents" are activated by addition of the substrate for the enzyme, such as methanol, glucose, or xanthine. Where required, a cosubstrate, such as oxygen, may also be supplied, together with any required cofactor, such as FAD.

It is also contemplated that the oxygen toxicity of the foregoing compounds may be enhanced by the concurrent administration of other materials with the antiproliferative agent. For example, myeloperoxidase with an oxidizable halide cofactor augments the toxicity effects of $H_2O_2$. Moreover, we know that oxygen toxicity of lens-associated tissue can be augmented by adding known inhibitors to the natural lens cellular defense mechanisms. The glutathione related defense seems to be most important in lens tissue. N,N-bis-(2-chloroethyl)-N-nitrosourea (BCNU) (0.1 mM) can be used to inhibit glutathione reductase. Similarly, buthione sulfoximine (BSO) (0.1 mM) can be used to inhibit glutathione synthesis.

In addition, alpha-emitting and beta-emitting radionuclides may be used. Such compounds include I-131, Yt-99, Cu-67, Ua-198, P-32 and other cytotoxic radionuclides.

A large number of direct acting antiproliferative agents are known, many of which can be conjugated to the antibodies of the present invention using known techniques. Simple screening procedures described herein can be used to determine the relative efficacy of the known agents. These agents includes folate inhibitors, pyrimidine analogs, purine analogs, alkylating agents and antibiotics. Specific examples of such antiproliferative agents include acivicin, aclarubicin, acodazole, adriamycin, ametantrone, aminoglutethimide, anthramycin, asparaginase, azacitidine, azetepa, bisantrene, bleomycin, busulfan, cactinomycin,, calusterone, caracemide, carboplatin, carmustine, carubicin, chlorambucil, cisplatin, cyclophosphamide, cytarabine, dacarbazine, dactinomycin, daunorubicin, dezaguanine, diaziquone, doxorubicin, epipropidine, etoposide, etoprine, floxuridine, fludarabine, fluorouracil, fluorocitabine, hydroxyurea, iproplating, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin. These compounds are all direct acting antiproliferatives; that is, they do not require activation or combination with another agent to form the active cytotoxic species.

Yet another category of direct acting compounds that may be bound to the antibodies of the present invention are toxins, such as ricin, tetanus, diphtheria, abrin, gelonin, mistletoe, pseudomonas exotoxin (either in its native form or as PE40, which has been modified by recombinant DNA technology to remove the binding domain), and other materials capable of causing localized necrosis.

C. Conjugation of Antiproliferative Agent to Antibody

The antiproliferative agent may be conjugated to the antibody using any of the well-known techniques for covalently linking proteins to other molecules. The particular technique chosen, of course, will depend on the characteristics of the antiproliferative agent.

For example, proteins may be covalently bound to other molecules through cyanogen bromide (CNBr) activation. These methods and others are described by Cuatrecasas, P., *Methods in Enzymology* 31: 345 (1969).

Additional methods for forming enzyme-antibody conjugates and other conjugates include the glutaraldehyde method described by Avrameas, et al., *Immunochemistry* 8: 1175–79 (1971); the periodic acid method as described by Nakane, et al, *Journal of Histochem. Cytochem.* 22: 1084–91 (1974); and the maleimide method, described by Monji, et al., *Biochem. Biophys. Res. Comm.* 85: 671 (1978). In particular, established crosslinking agents such as m-maleimidobenzoyl-N-hydroxysuccinimide ester, succinimidyl-4-(N-maleimidomethyl)-cyclohexane-1-carboxylate, N-succinimidyl-3-(2-pyridyldithio)proprionate, and N-succinimidyl-(4-iodoacetyl)aminobenzoate may be used. These amino or thio reactive agents can be used under mild coupling conditions at neutral pH with appropriate buffers to attach the ε-amino lysine groups or sulfhydryl groups on the surface of the proteins.

For example, free thiol groups may be introduced into the antibody by reacting antibody with N-succinimidyl-3-(2-pyridyldithio)propionate (SPDP) to introduce 2-pyridyl disulphide groups, which are reduced with dithiothreitol to leave free thiol groups. The protein to be bound to the antibody is incubated with SPDP. Upon mixing the SPDP-modified protein with the antibody containing free thiol groups, the two materials become bound.

Numerous other techniques are available for attaching various antiproliferative agents to antibodies. For example, many carboxylic acid-containing compounds (such as methotrexate) can be conjugated to immunoglobulins through an active ester intermediate, formed, e.g., by reacting the compound with N-hydroxysuccinimide and dicyclohexylcarbodiimide. See T. Deguchi, et al., *Effect of Methotrexate-Monoclonal Anti-Prostatic*

*Acid Phosphatase Antibody Conjugate on Human Prostate Tumor,* Cancer Res. 46: 3751-3755 (1986). The carboxyl-containing hematoporphyrin may be covalently bound to an amino group of the antibody with a cross linker such as 1-ethyl-3-(3-dimethylaminopropyl)-carbodiimide. Others, such as chlorambucil, will bind directly to the antibodies at low pH. See, e.g., T. Ghose, et al., *Immunochemotherapy of Human Malignant Melanoma with Chlorambucil-Carrying Antibody,* Europ. J. Cancer 11: 321-326 (1975). Ricin may be attached to antibody using m-maleimidobenzoyl-N-hydroxysuccinimide ester, as reported by R. Youle, et al., *Proc. Nat'l. Acad. Sci. USA* 77: 5483-86 (1980).

Amino sugar-containing drugs such as adriamycin and daunomycin may be covalently bound to antibodies by periodate oxidation of the drug, followed by linking of the oxidized drug to the immunoglobulin and subsequent reduction of the product with sodium borohydride. E. Hurwitz, et al., *The Covalent Binding of Daunomycin and Adriamycin to Antibodies,* Cancer Res. 35: 1175-1181 (1975).

Other known techniques, such as the use of dextran T-10 spacers to increase the number of drug moieties linked to antibody molecules, can be employed, as can mixed anhydride methods of drug conjugation. The compound 1-ethyl-3-(3-dimethylaminopropyl) carbodiimide hydrochloride (ECDI) may be used to bind amino-containing drugs to the carboxyl groups of antibodies. Alternatively, glutaraldehyde may be used for cross-linking between free amino groups of the antibody and amino groups in the compound to be conjugated thereto.

If it is desired to provide a radioactive antiproliferative, numerous methods are established for preparing the conjugates. Iodination, for example, may be accomplished using the chloramine-T method described by S. Mills, et al., $^{123}I$-*Radiolabeling of Nonoclonal Antibodies for In Vivo Procedures,* Hybridoma 5: 265-275 (1986). This technique may be used, e.g., to attach a radionuclide, such as I-125 or I-131.

Other radionuclides may be attached to the antibodies in question through chelation with benzyl EDTA or DPTA conjugation procedures. Still other suitable techniques include the iodogen method disclosed by M. Pimm, et al., i In Vivo Localization of Anti-Osteogenic Sarcoma 791T Monoclonal Antibody, 1 Int. J. Cancer 30: 75 (1982), and direct iodination with radioactive sodium iodide.

D. Screening of Conjugates for Activity

The relative activity of any particular antibodyantiproliferative agent conjugate may be determined by straightforward screening in in vivo or in vitro models.

After the conjugate to be screened is prepared in accordance with the foregoing disclosure, it is generally suspended in a saline or buffer solution at physiological pH. Fresh human or animal tissue containing the target cells may then be contacted with the conjugate solution, and rinsed after a suitable time for attachment of antibody (e.g., 30 minutes) to remove unbound conjugate. The bound conjugate is then activated in the appropriate manner, and after several minutes, the tissue is microscopically examined for cell lysis, or the tissue is monitored for cell lysis products, such as lactic dehydrogenase.

Where available, established cultures of target cells may be used in place of fresh tissue. This may be particularly advantageous when the antibodies are being developed to human tissue.

An in vivo screening procedure would involve removing the lens in an animal model (e.g., rabbit); injecting conjugate solution; activating after a suitable time for binding to take place has elapsed; and then monitoring for secondary cataract formation, with or without insertion of an intraocular lens.

E. Surgical Use of Immunoconjugates

Surgical removal of lens material in an animal model, or in a human, is accomplished using conventional extracapsular phacoemulsification techniques. An effective amount of the immunoconjugate composition of the present invention is then administered. (Because of differences in antibody affinity and activity of antiproliferative agents, the optimum dosage for any particular conjugate may be determined empirically. However, as a general rule, the dosage is calculated to deliver from approximately 0.1 to 100 $\mu$mols antiproliferative agent to each eye. Thus, for example, where the agent is hematoporphyrin, approximately 25 $\mu$mols antiproliferative agent may advantageously be delivered to each eye.)

After an appropriate time, generally between 1 and 100 minutes following administration of the conjugate, activation is accomplished by addition of a compound necessary for activation or exposure of the bound conjugate to an activator, such as light.

When hematoporphyrin is the antiproliferative agent, for example, it may advantageously be activated by exposure to laser light of an appropriate wavelength. One illustration of an appropriate laser system is a dye laser using dye marketed under the trade designation Kiton Red 620 by Exciton, Dayton, Ohio to emit radiation at 620 nm. A suitable dye laser is marketed by Coherent, Palo Alto, Calif., under the trade designation PRT-95 and emission may be stimulated with another laser, such as the argon-ion laser sold by Coherent under the trade designation NOVA 20. An appropriate activation may comprise directing the energy into the anterior chamber for a total exposure to about 1 to 15 $J/cm^2$. Alternatively, of course, any other suitable system providing electromagnetic energy of suitable wavelength may be used.

Photoactivation may be practiced as a one-shot procedure as a part of the surgery, with as little as 10 minutes permitted for localization of the antibody. Alternatively, the photoactivation of the antiproliferative agent may be accomplished after surgery by dilation of the pupil and exposure of lens area to laser light of appropriate wavelength. For example, postoperative exposure to activating light at one week, three months, and six months is believed to be advantageous.

When the antiproliferative agent is an enzyme, the substrate for that enzyme is added to produce the cytotoxic species. Thus, for example, glucose is added when the agent is glucose oxidase, and xanthine is added when the substrate is xanthine oxidase. Pure oxygen may be supplied to the patient or to the eye to facilitate the reaction. Moreover, trace amounts of $Fe+2$ in micromolar quantities are preferably added to catalyze the Haber-Weiss reaction. The reactions will be quenched in time with natural singlet oxygen quenchers, such as glutathione or superoxide dismutase and catalase.

After activation (if necessary) of the immunoconjugate, an intraocular lens may be implanted using established techniques. Alternatively, the lens may be implanted prior to activation, where activation will not be impaired by the presence of the lens. This alternative procedure may be particularly suitable for photoactivated antiproliferative agents.

The practice of certain aspects of the invention is more fully illustrated in the following examples:

EXAMPLE 1

Generation of Polyclonal Antibodies

Isolation of Lens Antigen:

For the isolation of crude plasma membranes, cortical or nuclear tissue from 300 rabbit lenses were obtained. Fiber masses were separated from the capsule and epithelium and homogenized in seven times the lens weight of 50 mM Tris-HCl (pH 7.4), 5 mM EDTA, 10 mM $\beta$-mercaptoethanol and 0.2% sodium azide (Buffer A). The material was centrifuged. All samples were centrifuged at 10000 x g for 20 minutes unless specifically noted. The pellet was rehomogenized in the Tris buffer and recentrifuged (2×). The pellets were rehomogenized in 7 M urea at pH 7.4 in 50 mM Tris-HCl (Buffer B): diluted 1:1 with water and centrifuged. The pellet was similarly treated 2×. The pellet was then homogenized in 0.1 M NaCl and 1 mM $\beta$-mercaptoethanol at 0° C. and allowed to stand for 15 minutes on ice. This fraction was centrifuged and the pellet resuspended in 5 mM phosphate at pH 8.0 for 10 minutes.

Preparation of Anti-MP26 Antiserum:

Anti-MP26 polyclonal antiserum was prepared by injecting intradermally an emulsion of the MP (lens-associated antigen) solution 2 mg in 1 ml of Freund complete adjuvant into the foot pads and back of a rabbit. Additional boosting was required at weekly intervals. The antiserum was isolated approximately three weeks later. During the immunizations, the antibody titers were monitored by ELISA assay and Western blots. The antisera and the conjugates were used in a dilution 1:10 of phosphate buffered saline (pH 7.2).

Preparation of membrane fractions from other ocular tissue followed similar procedures.

Anti-MP antibodies were purified on a column of Sepharose 4B conjugated with SDS-PAGE purified MP26 (see Paul and Goodenough, *J. Cell. Biol.* 96: 625 (1983) and Laemmli, *Nature* 227: 680 (1970)). Similar procedures were followed to remove undesired antigens from the epithelial polyclonal mixed antibody preparation.

EXAMPLE 2

Generation of Monoclonal Antibodies

Two-month old Balb/C mice are immunized with the 50$\mu$g antigen in Freund's complete adjuvant and boosted every week with the same amount in incomplete adjuvant. Eight weeks after the initial immunization, the same amount of antigen in PBS (phosphate buffered saline) is injected on three consecutive days. All injections are intraperitoneal (ip). Two days later, spleen cells from immunized mice are fused with NS-1 myeloma cells and directly cloned by limiting dilution according to established methods (see, e.g., Fazekas, et al., *J. Immunol. Methods* 35: 1 (1980); Staehli, et al., ibid 32: 297 (1980)). Hybridomas are initially screened for lens membrane specific monoclonal antibodies by ELISA assay and immunoblotting (Western). Hybridomas which give positive results in both assays are once more subcloned by limiting dilution to ensure their monoclonal character. Anti-MP antibodies are purified on a column of Sepharose 4B conjugated with SDS-PAGE purified MP26 (see Example 1).

Only hybridomas secreting antibodies that recognize membrane antigens in both the native, membrane bound conformation and the denatured form are maintained for further analysis.

EXAMPLE 3

Conjugation of Hematoporphyrin to Antibody

Twenty mg hematoporphyrin HCl in 1.25 ml of H$_2$O and 0.8 ml of N,N-dimethylformamide is added to 20 mg of 1-ethyl-3-(3-dimethylaminopropyl)carbodiimide-HCl in 0.6 ml H$_2$O. This is mixed with 15 mg of the polyclonal antibody serum from Example 1 dissolved in 5 ml of distilled H$_2$O and is maintained at a pH of between 6 and 7. Fifty $\mu$l or monoethanolamine is added to quench the reaction. Conjugated material is then dialyzed repeatedly against 0.001 N phosphate buffered saline (pH 7.4) at 4° C. Activity of the hematoporphyrin following conjugation is tested by assaying its ability to lyse red blood cells, and antibody activity is measured by reactivity in ELISA assays.

EXAMPLE 4

Preparation of Monoclonal Antibody Conjugate

The procedure of Example 3 is repeated with the monoclonal antibody of Example 2. Similar results are achieved.

EXAMPLE 5

Conjugation of Glucose Oxidase to Antibody

Approximately 50$\mu$g of the purified IgG monoclonal antibody is reacted with 150 $\mu$moles glucose oxidase and sulfosuccinimidyl 4-(N-maleimidomethyl)cyclohexane1-carboxylate in a 2:1 molar excess at pH 8.0 borate buffer for 30 minutes. This reaction crosslinks the $\epsilon$-amino groups for the covalent formation of the immunotoxin. The crude immunotoxin (glucose oxidase-monoclonal antibody) is dialyzed and subsequently purified on an affinity column of Protein-A (Pharmacia). The degree of modification is established by immunoblot following the generation of H$_2$O$_2$ with 2,6-dichlorophenolindophenol. The immunotoxin is used as a 100:1 dilution on the target cells for prevention of anti-proliferation.

EXAMPLE 6

In Vivo Administration of Hematoporphyrin Conjugate

Rabbits are anesthetized with approximately 5 mg/kg aseptic promazine and 50 mg/kg xylazine. The eye is dilated with 1% cyclogyl and 2.5% neo-synephrine. The eyelashes are trimmed and the eye is prepped with betadine periocularly. A wire lid speculum is inserted to retract the eyelids and a binocular microscope is brought into place.

A corneo-scleral incision is made at approximately 11:00 limbus with a microsharp blade and is enlarged to 3 mm with curved corneal scissors.

A phacoemulsification tip is inserted through the corneo-scleral wound and is used to perform a small anterior capsulotomy and remove the nucleus of the lens using balanced salt solution (BSS) irrigating solution. Following phacoemulsification, an irrigation/aspiration tip is then used to remove the lens cortex completely. With low vacuum suction, residual lens epithelial cells are removed from the anterior capsule. (This procedure could similarly be practiced on the human eye, which would entail anterior capsulotomy prior to the phacoemulsification procedure and the subsequent placement of the prosthesis intraocular lens (IOL).)

The conjugate of Example 4 is diluted 100:1 in sterile saline solution. Following removal of the rabbit lens, 0.1 ml of this solution is injected through a 23-27 gauge cannula into the lens capsular bag (or alternatively is included in the viscous material, such as hyaluronic acid, used in the phacoemulsification procedure and/or included during irrigation as an additive in the BSS), with some leakage into the anterior chamber. After approximately 10 minutes (for the immunoconjugate to bind to the target lens-associated cells), the eye is exposed to 620 nm light from a dye laser through an endo-light probe at a delivered power intensity of 120 milliwatt/cm for 1 minute to activate the hematoporphyrin and destroy the bound cells. The corneo-scleral incision is then closed with 10-0 nylon suture. This treatment is effective over a period of at least six months in preventing secondary cataract formation.

What is claimed is:

1. A method for preventing tissue growth in the eye following removal of the natural lens, comprising the steps of:
    providing an antibody specific to proliferative cells in the lens capsular bag and anterior chamber, but not to other eye tissue, wherein said antibody is conjugated to an antiproliferative agent, wherein said antiproliferative agent requires activation in order to prevent proliferation of cells bound by said antibody conjugate;
    introducing said antibody into the lens capsular bag or anterior chamber of the eye after removal of the natural lens from the eye;
    permitting said antibody conjugate to bind to proliferative cells in the lens capsular bag or anterior chamber; and
    activating said proliferative agent after binding said cells to prevent proliferation of said bound cells.

2. The method of claim 1, wherein said antiproliferative agent is activated by cooperating with a second compound to form an active proliferationpreventative species, and wherein said activating step comprise adding said second compound to said lens capsular bag and interior chamber.

3. The method of claim 2, wherein said antiproliferative agent is an enzyme and said second compound is a substrate for said enzyme, and wherein action of said enzyme on said substrate generates said proliferation-preventative species.

4. The method of claim 3, wherein said enzyme is xanthine oxidase or glucose oxidase.

5. The method of claim 1, wherein said antiproliferative agent requires activation by light in order to prevent proliferation of said bound cells, further comprising the step of:
    activating said antiproliferative agent with light after binding said cells.

6. The method of claim 2 or 5, wherein said antiproliferative agent forms an oxidizing moiety after activation to prevent proliferation of said cells.

7. The method of claim 1, wherein said antibody is polyclonal antibody.

8. The method of claim 1, wherein said antibody is monoclonal antibody.

9. The method of claim 6, wherein the light required to activate said antiproliferative agent is light of a certain wavelength, and wherein said activation step comprises directing light of said wavelength into the eye.

10. The method of claim 5, wherein said antiproliferative agent is hematoporphyrin.

11. The method of claim 7 or 8, wherein said antibody is specific to lens epithelial cell surface antigen.

12. The method of claim 7 or 8, wherein said antibody is specific to lens fiber cell surface antigen.

13. The method of claim 12, wherein said antigen is a protein of about 26,000 daltons.

14. The method of claim 12, wherein said antigen is a protein of about 70,000 daltons.

15. A method for preventing tissue growth in the eye following removal of the natural lens, comprising the steps of:
    providing an antibody specific to proliferative cells in the lens capsular bag and anterior chamber but not to other eye tissue, wherein said antibody is conjugated to an antiproliferative agent requiring activation by light in order to prevent proliferation of said cells;
    introducing said antibody directly into the lens capsular bag and anterior chamber of the eye after removal of the natural lens therefrom;
    permitting said antibody to bind to proliferative cells in the lens capsular bag and anterior chamber;
    activating said antiproliferative agent after binding said cells by directing light into the eye; and
    preventing proliferation of said bound cells with said antiproliferative agent.

16. A composition for preventing tissue ingrowth into the lens capsule or anterior chamber of the eye following removal of the natural lens, comprising:
    an antibody that is specific to a cell surface antigen of proliferative cells in the lens capsule or anterior chamber, but not specific to other ocular tissue; and
    an antiproliferative agent that must be activated in order to exhibit antiproliferative properties conjugated to said antibody for preventing growth of said proliferative cells.

17. The composition of claim 16, wherein said antiproliferative agent is activated by cooperating with a second compound to form a proliferation-preventative species.

18. The composition of claim 16, wherein said antibody is polyclonal antibody.

19. The composition of claim 16, wherein said antibody is monoclonal antibody.

20. The composition of claim 18 or 19, wherein said antibody is specific to lens epithelial cell surface antigen.

21. The composition of claim 18 or 19, wherein said antibody is specific to lens fiber cell surface antigen.

22. The composition of claim 21, wherein said antigen is a protein of about 26,000 daltons.

23. The composition of claim 21, wherein said antigen is a protein of about 70,000 daltons.

24. THe composition of claim 17, wherein said antiproliferative agent is an enzyme and said second compound is a substrate for said enzyme, and wherein action of said enzyme on said substrate generates said proliferation-preventative species.

25. The composition of claim 26, wherein said enzyme is xanthine oxidase or glucose oxidase.

26. A composition for preventing tissue ingrowth into the lens capsule or anterior chamber of the eye following removal of the natural lens, comprising:
- an antibody that is specific to a cell surface antigen of proliferative cells in the lens capsule or anterior chamber, but not specific to other ocular tissue; and
- an antiproliferative agent, which must be activated by light in order to exhibit antiproliferative properties, conjugated to said antibody for preventing growth of said proliferative cells.

27. The composition of claim 16 or 26, wherein said antiproliferative agent forms an oxidizing moiety to prevent proliferation of said cells after activation.

28. The composition of claim 26, wherein said antiproliferative agent forms an oxidizing moiety to prevent proliferation of said cells and wherein light of a certain wavelength is required to activate said antiproliferative agent.

29. The composition of claim 26, wherein said antiproliferative agent is hematoporphyrin.

* * * * *